(12) United States Patent
Alexander et al.

(10) Patent No.: US 9,297,756 B2
(45) Date of Patent: Mar. 29, 2016

(54) CAPILLARY ABSORPTION SPECTROMETER AND PROCESS FOR ISOTOPIC ANALYSIS OF SMALL SAMPLES

(71) Applicants: M. Lizabeth Alexander, Richland, WA (US); James F. Kelly, Pasco, WA (US); Robert L. Sams, Kennewick, WA (US); James J. Moran, Richland, WA (US); Matthew K. Newburn, West Richland, WA (US); Thomas A. Blake, Kennewick, WA (US)

(72) Inventors: M. Lizabeth Alexander, Richland, WA (US); James F. Kelly, Pasco, WA (US); Robert L. Sams, Kennewick, WA (US); James J. Moran, Richland, WA (US); Matthew K. Newburn, West Richland, WA (US); Thomas A. Blake, Kennewick, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 446 days.

(21) Appl. No.: 13/757,460

(22) Filed: Feb. 1, 2013

(65) Prior Publication Data
US 2014/0220700 A1    Aug. 7, 2014

(51) Int. Cl.
*G01N 21/00* (2006.01)
*G01N 21/59* (2006.01)
*G01J 3/433* (2006.01)
(Continued)

(52) U.S. Cl.
CPC ............... *G01N 21/59* (2013.01); *G01J 3/4338* (2013.01); *G01N 21/3103* (2013.01); *G01N 21/39* (2013.01); *G02B 6/4296* (2013.01); *G01N 21/3504* (2013.01); *G01N 21/718* (2013.01); *G01N 2021/0346* (2013.01); *G01N 2021/052* (2013.01); *G01N 2021/3125* (2013.01); *G01N 2021/399* (2013.01); *G01N 2021/8578* (2013.01); *G02B 6/02328* (2013.01)

(58) Field of Classification Search
CPC . G01N 21/3504; G01N 33/497; G01N 21/39; G01N 2021/399; G01N 21/031; G01N 21/276; G01N 33/58; G01N 21/00; G01N 21/65; G01N 33/0004; G01N 33/02; G01N 2021/3595; G01N 21/314; G01N 21/3563
See application file for complete search history.

(56) References Cited

U.S. PATENT DOCUMENTS 5,957,858 A    9/1999    Micheels et al.

FOREIGN PATENT DOCUMENTS

WO    9942814    8/1999
WO    2007008932 A2    1/2007
(Continued)

OTHER PUBLICATIONS

Schulze et al. "Laser ablation-combustion-GC-IRMS Laser ablation-combustion-GC-IRMS—a new method for online analysis of intra-annual variation of δ13C in tree rings", Tree Physiology, 2004, v. 24, pp. 1193-1201.*
Moran et al. "Laser ablation isotope ratio mass spectrometry for enhanced sensitivity and spatial resolution in stable isotope analysis" Rapid Commun. Mass Spectrom. 2011, v. 25, pp. 1282-1290.*
(Continued)

*Primary Examiner* — Yelena G Gakh
(74) *Attorney, Agent, or Firm* — James D. Matheson (57) ABSTRACT

A capillary absorption spectrometer and process are described that provide highly sensitive and accurate stable absorption measurements of analytes in a sample gas that may include isotopologues of carbon and oxygen obtained from gas and biological samples. It further provides isotopic images of microbial communities that allow tracking of nutrients at the single cell level. It further targets naturally occurring variations in carbon and oxygen isotopes that avoids need for expensive isotopically labeled mixtures which allows study of samples taken from the field without modification. The method also permits sampling in vivo permitting real-time ambient studies of microbial communities.

8 Claims, 7 Drawing Sheets

(51) Int. Cl.
- *G01N 21/31* (2006.01)
- *G01N 21/39* (2006.01)
- *G02B 6/42* (2006.01)
- *G01N 21/3504* (2014.01)
- *G01N 21/71* (2006.01)
- *G02B 6/02* (2006.01)
- *G01N 21/03* (2006.01)
- *G01N 21/05* (2006.01)
- *G01N 21/85* (2006.01)

(56) References Cited

FOREIGN PATENT DOCUMENTS

| WO | 2007008932 A3 | 1/2007 |
|---|---|---|
| WO | 2012018869 A1 | 2/2012 |
| WO | 2012031208 A2 | 3/2012 |

OTHER PUBLICATIONS

Nelson et al. "New method for isotopic ratio measurements of atmospheric carbon dioxide using a 4.3 μm pulsed quantum cascade laser", Appl. Phys.B, 2008, v. 90, pp. 301-309.*

Blake et al. "Absorption spectroscopy in hollow-glass waveguides using infrared diode lasers", Proceed. SPIE, 2002, v. 4817, pp. 216-232.*

Zare et al. "High-precision optical measurements of 13C/12C isotope ratios in organic compounds at natural abundance", PNAS, 2009, v. 106, No. 27, pp. 10928-10932.*

International Search Report/Written Opinion for International Application No. PCT/US2013/069705, International Filing Date Nov. 2, 2013, Date of Mailing Feb. 14, 2014.

Kelly, J. F., et al., A capillary absorption spectrometer for stable carbon isotope ratio (13C/12C) analysis in very small samples, Review of Scientific Instruments, 83, 2012, 023101-01-023101-14.

* cited by examiner

CAPILLARY ABSORPTION SPECTROMETER AND PROCESS FOR ISOTOPIC ANALYSIS OF SMALL SAMPLES

STATEMENT REGARDING RIGHTS TO INVENTION MADE UNDER FEDERALLY-SPONSORED RESEARCH AND DEVELOPMENT

This invention was made with Government support under Contract DE-AC05-76RLO1830 awarded by the U.S. Department of Energy. The Government has certain rights in the invention.

FIELD OF THE INVENTION

The present invention relates generally to laser spectroscopy systems and methods for detection of isotopologues. More particularly, the present invention relates to a laser ablation capillary absorption spectrometer and process for determination of isotopologues in small (e.g., picomolar or sub-picomolar) samples.

BACKGROUND OF THE INVENTION

Isotope ratio (IR) mass spectrometry (MS) (i.e., IRMS), and laser ablation (LA) mass spectrometry (MS) (i.e., LAMS) are conventional approaches for detecting isotopes. These systems typically involve converting laser ablated material into carbon dioxide or carbon monoxide, which species are then measured with a mass spectrometer to provide an isotope ratio for analytes of interest. Tunable IR laser absorption spectroscopies can measure raw isotopic differences for many different gaseous samples at precisions better than 0.2‰. And, they can offer a natural means to avoid isobaric interferences ($^{14}N^{14}N^{16}O$, $^{16}O^{12}C^{16}O$, and etc.) because the IR absorption transitions are quite specific to molecular structure. In fact, even pure isomers including rearrangement isotopologues such as $^{14}N^{15}NO$ and $^{15}N^{14}NO$, etc. can be readily distinguished with tunable IR laser absorption spectroscopy. Laser-based isotope discriminators are also being developed to handle a variety of gaseous compounds since much less sample preparation is needed to isolate isobaric interferences. And, laser-based systems and methods can offer more flexibility in performing real-time or near real-time isotopic analyses of atmospheric gas samples in the field with direct ingestion of mixed gas samples. However, most commercial laser absorption-based devices are designed for fast in situ analyses of ambient gases. And, with long pathlength absorption cells, such systems suffer significant sample dilution. Further, while commercial IRMS systems are available for measuring $CO_2$ isotopic differences, conventional optical cavity architectures currently require more than ~100 nanomoles of $CO_2$ to be effective. The technical literature reports best case minimum detectable absorbance (MDA) values for continuous-wave-QC laser systems used in concert with compact IR cavity ring down spectroscopies of about $2.2 \times 10^{-8}$. Furthermore, while IR absorption in multi-pass or ring-down optical gas cells has been applied to stable isotope measurements, only a fraction of a sample can be ablated by the laser and released into the multi-pass or ring-down cavity in these systems. Given that analyses in these systems require about 200 to 300 nanomoles of sample, isotopic imaging at a 1 micron resolution is precluded. Secondary Ion Mass Spectrometry (SIMS) can also provide data similar to those obtained with laser ablation, but at a cost that is at least ten times greater and a throughput that is lower. SIMS also requires substantial sample preparation and must be performed under ultra-high (e.g., $10^{-7}$ Torr or less) vacuum conditions, which have the potential to alter the sample, and further precludes any in vivo studies. Accordingly new systems, devices, and processes are needed that enable determination of stable isotopes at the single cell level or better. The present invention addresses these needs.

SUMMARY OF THE INVENTION

The present invention includes a new laser ablation capillary absorption spectrometer (LA-CAS) and process that provide highly sensitive (i.e., detection of molecular isotopologues at quantities down to 100 femtomoles) and accurate (0.5‰ or better) stable measurements of molecular isotopologues in small samples containing down to 100 femtomoles of material including samples containing biological materials (e.g., 1 to 10 cells).

The present invention includes an optical isolation device that couples to an excitation laser and an absorption (or transmission) device.

The optical isolation device may include a turbulence generator that induces a random spatial and temporal variation in the index of refraction of a medium through which a light beam from the laser is delivered as a function of time.

The medium may be a gaseous medium, a liquid medium, an aerosol-containing medium, a particulate-containing medium, and combinations of these various media.

Turbulence generators may include, but are not limited to, e.g., heat sources, gas sources, forced gas sources, forced air sources, flowing gas sources, flame sources, sonic sources, liquid sources, forced liquid sources, flowing liquid sources, including combinations of these various devices.

The optical isolation device may include an aerosol or particulate generator that delivers a distribution of aerosols and particulates of selected sizes and velocities into a medium through which a light beam from the laser is delivered as a function of time. The distribution of aerosols and particulates in the medium may induce a random spatial and temporal variation in divergence angle and pointing angle of the excitation beam when delivered through the medium. Aerosol and particulate generators include, but are not limited to, e.g., aerosol delivery devices, nebulizing devices, particulate delivery devices, including combinations of these various devices.

The optical isolation device may be positioned adjacent the excitation laser in front of the absorption or transmission device.

The optical isolation device may include a heat source configured to deliver turbulent air at a selected "dither" (i.e., variable and random) frequency at one or more selected temperatures across the propagation (optical) path of the excitation beam delivered through a medium to optically isolate the excitation laser from light reflected back to the laser from an optically coupled absorption (or transmission) device.

The optical isolation device may be a sonic device configured to deliver a random spread of sonic waves through a medium at a plurality of temperatures above ambient across the propagation path of the excitation beam emitted from the laser that provides a random spatial and temporal variation in the index of refraction of the medium through which the excitation beam is delivered en route to the absorption device and/or the transmission device when directed through the spread of sonic waves.

The optical isolation device may deliver a turbulent gas or a turbulent liquid through a medium across the propagation path of the excitation beam emitted from the laser that provides a random spatial variation in the index of refraction of the medium through which the excitation beam is delivered through the turbulent gas or the turbulent liquid to the absorption device or the transmission device.

The optical isolation device may deliver turbulent air at a temperature selected in the range from about 150° C. to about 400° C.

The optical isolation device may include an enclosed liquid that is coupled to a turbulence generator. The turbulence generator provides a turbulent liquid that provides a random spatial and temporal variation in the index of refraction of the light beam when delivered to the absorption device or the transmission device through the turbulent liquid.

The optical isolation device may be a sonic device configured to deliver a random spread of sonic waves in a medium at a plurality of temperatures above ambient across the propagation path of the light beam from the laser that provides a random spatial and temporal variation in the index of refraction of the medium when light from the laser is directed through the spread of sonic waves in the medium.

One or more spatial filters may be positioned adjacent the optical isolation device at a tilt angle that selects a subset of rays from the excitation beam at a selected pointing angle and selected beam spread into the absorption or transmission device. The spatial filtering devices may deliver the excitation beam off-axis to the absorption or transmission device.

Spatial filtering devices include, but are not limited to, e.g., lenses, slits, pin holes, or combinations of these various devices.

The optical isolation device may randomize the spread of the excitation beam wave fronts delivered through a medium to the absorption or transmission device to eliminate feedback noise stemming from reflections and/or scatter in the excitation beam returning back to the excitation laser.

The medium through which the light beam is delivered may be a gaseous medium, a liquid medium, an aerosol-containing medium, a particulate-containing medium, and combinations thereof.

The optical isolation device can randomize the pointing angle and the spread of the light beam delivered to the absorption (or transmission) device to provide the random spatial variation as a function of time that suppresses feedback noise induced by reflection of the light beam incident upon and/or from within the absorption or the transmission device back to the laser device.

The optical isolation device can provide a signal-to-noise ratio for an absorption sensitivity measurement obtained from the absorption device and/or a transmission sensitivity measurement obtained from the transmission device that is enhanced by a factor of at least 10 times compared to a system or device absent the optical isolation device.

The randomizing source may be an aerosol source configured to deliver a random spread of aerosols with a random distribution of sizes and velocities across the propagation path of the light beam when the light beam is directed through the spread of aerosols in the medium to the absorption device or the transmission device.

The optical isolation device may be a vapor-nebulizing device configured to deliver a random spread of aerosols of a selected size at a plurality of angles and/or a plurality of temperatures above ambient across the propagation path of the light beam that provides the random spatial variation in the index of refraction of the light beam delivered to the absorption device and/or the transmission device when directed through the spread of aerosols.

The optical isolation device may include an enclosed liquid maintained at a random temperature above ambient that provides a random spatial and temporal variation in the index of refraction of a medium through which the excitation beam is delivered en route to the absorption device or the transmission device when directed through the liquid.

The medium may include an open volume or an enclosed volume.

The present invention also includes a capillary absorption spectrometer (CAS) that provides sensitive, accurate, and stable isotope measurements in small samples including those containing biological materials down to a single cell level. The CAS spectrometer may include: an excitation laser configured to supply a non-pulsed excitation beam to an absorption device. The absorption device may include an absorption volume configured to receive a sample gas containing analytes therein that absorb in the infra-red region when an excitation beam from an excitation laser is introduced therein.

The spectrometer may include a (signal) modulation device configured with a second or higher order bias-T (diplexer) that couples to the excitation laser. The bias-T may suppress harmonics from a repetitive linear current ramp source and sub-harmonics from a dither-modulated current source in the modulation device such that the amplitude of the harmonics and the sub-harmonics is at least 60 dB lower than the modulation waveform selected and provided to the excitation laser.

The modulation device may deliver a frequency (f)-modulated excitation beam to the absorption or transmission device, where (f) is ½ the in-quadrature condition of the residual amplitude modulation (RAM) distortion frequency (response) of a semiconductor laser.

The spectrometer may also include an optical isolation device that is positioned between the excitation laser and an absorption device. The optical isolation device may randomize the pointing angle and the spread of the excitation beam that suppresses feedback noise induced by reflection of the excitation beam incident upon, and from within, the absorption device back to the excitation laser. The spectrometer may also include a detection device that couples to the absorption device and configured to detect absorption features for one or more analytes when present in the sample gas introduced in the absorption device.

The CAS spectrometer may provide a molar sensitivity of between about 10 nanomoles and about 100 femtomoles for isotopic ratio measurements. The CAS spectrometer may provide a precision for isotopic ratio measurements of at least about 2‰ or better.

The CAS spectrometer may include a laser ablation device that is coupled to a catalytic reactor that is coupled to a transfer device. The laser ablation device is configured to deliver ablated sample particulates to the catalytic reactor for combustion therein. The catalytic reactor is configured to convert the sample particulates received from the ablation device into at least one molecular gas. The transfer device is configured to transfer the at least one molecular gas into the IR absorption device for analysis therein.

The spectrometer may include a laser ablation device and a catalytic reactor coupled to the IR absorption device.

The method may include introducing a sample to the ablation device in a carrier gas. The carrier gas may include or be composed of, e.g., air, nitrogen, argon, helium, oxygen, carbon dioxide, and combinations of these various gases. The carrier gas may also be a $CO_2$-containing gas.

The catalytic reactor may be configured to oxidize or reduce a target element selected from C, N, O, S, P including combinations of these elements present in the sample received from the laser ablation device that yields gas-phase molecular species in a form that can be probed by IR absorption. Gas-phase molecular species include species: 1) suitable for IR absorption when introduced into the IR absorption device, or 2) that provide a sufficient IR absorption signal when introduced into the IR absorption device that permits determination of elemental ratios for isotopes therein.

The laser ablation device may be configured to ablate a small sample defined by a quantity of material down to 100 femtomoles into particulates. The catalytic reactor may be configured to oxidize or reduce particulates received from the laser ablation device and combust the particulates to convert same to one or more molecular gases. The absorption device may be configured to measure the absorption signal of target elements in the combusted gas sample received from the catalytic reactor and provide an isotopic ratio measurement of the target elements in the sample with a precision of at least about 2‰ or better.

The transfer device may transfer analytes from the catalytic reactor at a first (high) pressure and deliver the analytes into the absorption device at a $2^{nd}$ (lower) pressure without a loss of analytes.

The transfer device may be a conduction-limited transfer device that provides continuous transfer of analytes from the catalytic reactor at the first (high) pressure to the IR absorption device at the second (lower) pressure in concert with a graded reduction in pressure.

The transfer device may be a cryogenic transfer device. The cryogenic transfer device may include a cryogenic trap. The cryogenic trap may be configured 1) to receive analytes from the catalytic reactor at the first (high) pressure and to simultaneously condense and trap the analytes therein, 2) to isolate and evacuate the transfer device to match the second (lower) pressure of the absorption device, and 3) to evaporate and transfer the analytes into the absorption device at the second (lower) pressure. The cryogenic transfer device may be configured to cycle the pressure between the first (high) pressure that matches the output pressure of the catalytic reactor while cryogenically trapping the analyte in the cryogenic trap and the second (lower) pressure and evaporating the sample while simultaneously transferring the analyte into the absorption device at the second lower pressure that matches the input pressure of the IR absorption device.

The first pressure may be selected from about 100 Torr (0.13 atm) and about 760 Torr (1 atm). The second ($2^{nd}$) pressure may be selected from about 25 Torr (0.03 atm) or below. In some applications, the $2^{nd}$ pressure may be selected from about 1 Torr (0.001 atm) to about 25 Torr (0.03 atm).

The excitation laser may be a continuous-wave laser.

The CAS spectrometer may include one or more spatial selection or filtering devices positioned to deliver the excitation beam from the excitation laser off-axis to the absorption device through the medium of the optical isolation device to suppress reflections of light from the absorption device back to the excitation laser.

The absorption device may be a capillary optical waveguide. The absorption device may be a tapered hollow wave guide with an internal diameter that varies as a function of length, or an optical fiber with an internal diameter that is a fixed diameter. The absorption device may be a hollow wave guide having dimensions of about 1-mm ID with a physical path length of about 0.8 meter.

The absorption device may include an absorption volume at or below 10 cm³. The absorption device may include an optical path length of about 10 cm or greater.

The absorption device may be configured to contain a total gas pressure at or below 25 Torr (0.03 atm). The total gas pressure may be a combined pressure for the sample gas plus the carrier (or buffer) gas.

The absorption device may be configured to receive a sample gas containing one or more analytes therein.

The detection device may be configured to resolve 1f or 2f absorption signals of one or more analytes introduced in a sample gas to the capillary absorption (or transmission) device.

The modulation device may include a dither-modulated current source that delivers a dither-modulated frequency. The dither-modulated frequency may be tuned to a frequency that is one-half (½) the Residual Amplitude Modulation (RAM) distortion frequency (response) of the excitation laser. Tuning refers to the process in which the frequency of a receiver circuit of a detector of may be continuously adjusted (e.g., over a frequency range being scanned) to locate a frequency where analytes absorb and where the frequency of the absorption signal of the selected analyte(s) may be detected.

The modulation device may include both a repetitive linear current ramp source and a dither-modulated current source. The modulation device may be configured to deliver frequencies that are non-integer fractions of fundamental reference frequencies of these respective sources. The non-integer frequencies delivered by the modulation device may suppress cross talk arising from overlapping phase and/or frequency differences between the repetitive linear current ramp source and the dither-modulated current source.

The repetitive linear current ramp source may deliver a frequency that is at least a factor of 5 below the frequency delivered by the dither-modulated current source.

The detection device may include a phase-sensitive detection circuit. The phase-sensitive detection circuit may include a first circuit segment having a Diplexer configured to deliver a detection signal from the absorption device as an input to a double-balanced mixing device, and a second circuit segment having a Band-Pass Filter (BPF) configured to deliver a reference (drive) signal free of harmonic and intermodulation distortion from the dither-modulated current source of the modulation device as a separate input to the double-balanced mixing device. The double-balanced mixing device may deliver an output signal made up of various combinations of the signals (i.e., mixed signals) received from the respective inputs.

The double-balanced mixing device (DBM) may couple to a $2^{nd}$ or greater order Diplexer (bias-T) that is configured to 1) receive the mixed output signal from the DBM as an input and 2) to isolate a selected absorption response signal for one or more selected analytes present in the mixed signal.

The $2^{nd}$-order or greater Diplexer of the phase-sensitive detection circuit may be configured to receive an output signal from the double balanced mixing device and to deliver a distortion free response signal as an output therefrom at a selected frequency.

The $2^{nd}$-order or greater Diplexer may deliver the isolated response signal at 1-times (1f) or 2-times (2f) the dither-modulated frequency of the modulation device and that is 90 degrees out-of-phase with the RAM distortion frequency of the excitation laser.

The $2^{nd}$-order or greater Diplexer may deliver a response signal with a frequency selected in the range from about 100 Hz to about 30 KHz with an isolation of about 30 dB per decade at the upper cutoff frequency.

The phase-sensitive detection circuit may suppress noise in the absorption signal arising from the RAM distortion frequency received from the excitation laser and from harmonic distortion frequencies received from the dither-modulated current source.

The present invention also includes a method for analyzing a sample. Samples may include low-volume of solid samples. The method may include ablating a picomolar quantity of a solid sample with a pulsed UV excitation beam to convert the sample into sample particulates. The ablated sample particulates may be passed to a catalytic reactor. The ablated sample particulates may be combusted in the catalytic reactor to convert the ablated sample particulates into a molecular gas. The molecular gas from the catalytic reactor may be transferred through a transfer device at a first higher pressure into a capillary IR absorption device at a second lower pressure.

The capillary IR absorption device for measurements of a quantity of a target element less than 1 picomole may include a volume between about 0.1 cm$^3$ and about 1 cm$^3$.

The sample in the absorption device may be analyzed with a capillary absorption spectrometer in concert with an IR absorption detector to determine isotopic ratios of analytes in the sample. The sample may be analyzed in the IR absorption device by probing with an IR laser beam. The analytes in the sample may be detected with an IR absorption detector.

The detector may be an infra-red sensitive detector. In some applications, the detector is an indium-antimonide (InSb) detector.

The sample may be a biological isolate containing at least one single cell. Analyses may be performed in vivo at ambient conditions in real-time. The in vivo analyses may yield isotopic images of microbial samples that allows tracking of nutrients in the microbial sample at the single cell level as a function of time.

Analyses may include a lower limit of detection for an isotope-containing sample gas down to a pressure of about 2 Torr (0.003 atm).

The method may include calibrating the spectrometer with a solid calibration standard. The calibration may be performed with a solid sample referenced to a known standard. The solid calibration standard may include a polymer. The calibration may include introducing the solid isotopic or elemental standard into the laser ablation device to form particulates that when introduced into the catalytic reactor form molecular species that are the same as the analytes in the sample to be determined. The calibration may provide real-time, isotopic calibration of the spectrometer that allows determination of the isotopic ratio of analytes in the sample. The calibration may include calibrating with a normalization method.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

DETAILED DESCRIPTION

A new laser ablation capillary absorption spectrometer (LA-CAS) and process are described that provide highly sensitive (down to 100 femtomoles) and accurate (0.2‰ or better) stable isotope measurements of molecular isotopologues present in samples including samples containing biological and other organic materials. The term "isotopologue" as used herein refers to molecular species that differ only in their isotopic composition, i.e., the number of isotopic substitutions. Each member of an isotopologue family has at least one atom with a different number of neutrons than the parent molecule. Water, as an example, has isotopologues that include: light water (HOH or $H_2O$); "semi-heavy water" with the deuterium isotope present in equal proportion to protium (HDO or $^1H^2HO$); "heavy water" with two deuterium isotopes of hydrogen per molecule ($D_2O$ or $^2H_2O$); and "super-heavy water" or tritiated water ($T_2O$ or $^3H_2O$), where hydrogen atoms are replaced with tritium isotopes. Oxygen-related isotopologues of water include heavy-oxygen water ($H_2^{18}O$) and the slightly lighter isotopologue containing the $^{17}O$ isotope, ($H_2^{17}O$). In the doubly labeled water isotopologue, both oxygen (O) and hydrogen (H) are replaced by isotopes ($D_2^{18}O$). Further aspects of the present invention are detailed in a publication by Kelly et al. in [*Review of Scientific Instruments* 83, 023101 (2012)], which reference is incorporated herein in its entirety. The following description includes a best mode of at least one embodiment of the present invention. It will be clear from this description that the invention is not limited to these illustrated embodiments but that the invention also includes a variety of modifications and embodiments thereto. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims. Therefore the present description should be seen as illustrative and not limiting.

LA-CAS Spectrometer

Figure 1:
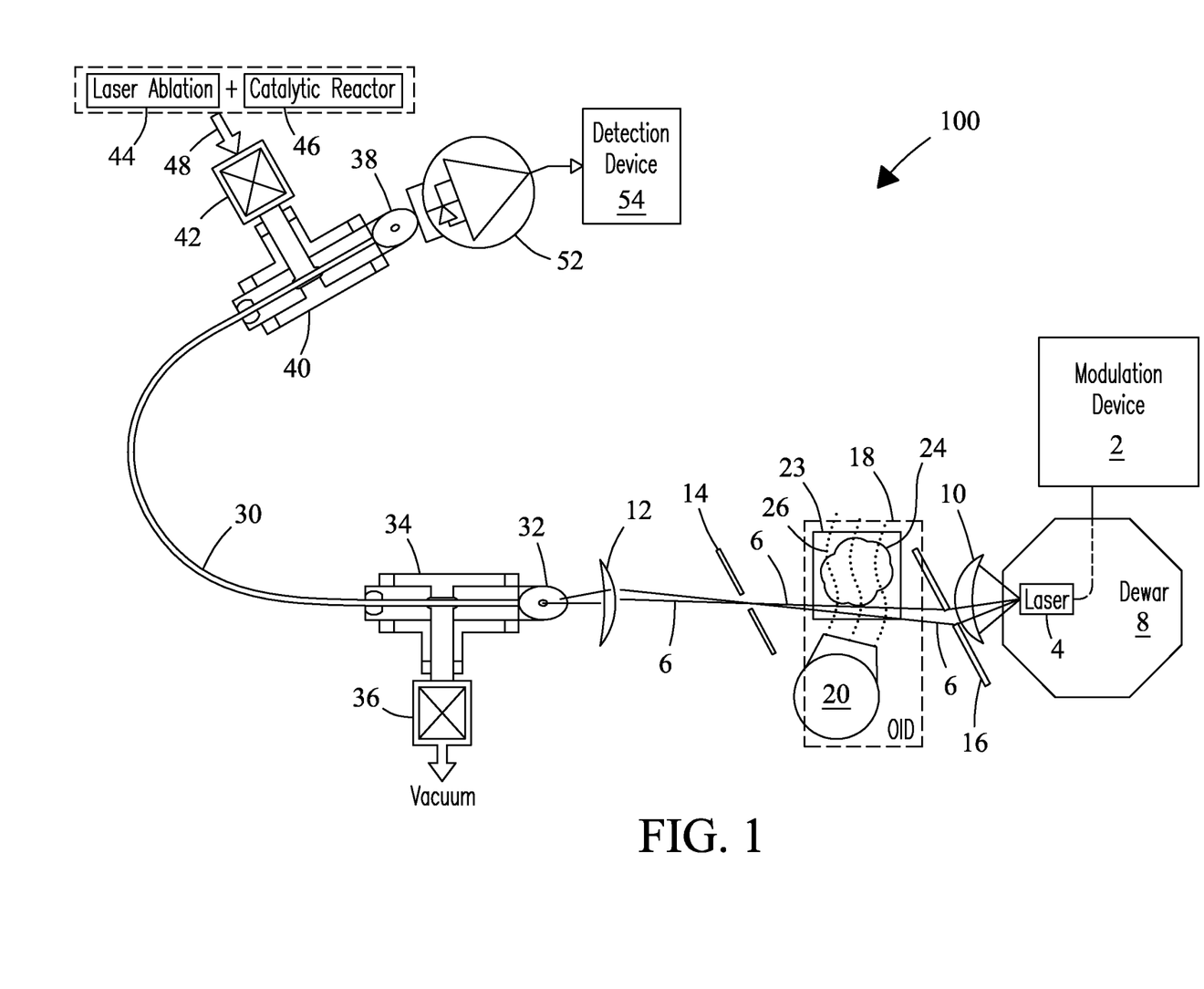
FIG. 1 is a schematic illustrating exemplary components of a capillary absorption spectrometer (CAS) of the present invention.

FIG. 1 is a schematic showing a laser ablation (LA) capillary absorption spectrometer (LA-CAS) 100 of the present invention. LA-CAS spectrometer 100 may include a modulation device 2 coupled to an excitation laser 4. Modulation device 2 may be configured to deliver a current-controlled waveform to excitation laser 4. Excitation laser 4 may be configured to supply a non-pulsed excitation beam 6 to an absorption (or transmission) device 30. The current-controlled waveform 6 may include: a DC offset current that establishes the initial frequency of beam 6 emitted from laser 4, a repetitive linear current ramp (i.e., repeated cycles of up and down ramping) that sets the range over which the frequency of laser 4 is scanned that may be added to or superimposed atop a dither-modulated current that serves to modulate the output frequency of beam 6 emitted from laser 4. The output frequency of beam 6 may be modulated around a center value determined by the sum of the DC offset current and the linear ramped current as a function of time. "Dither-modulated" as used herein means a variation in a selected frequency that is on the order of the transition line width relative to the total frequency range being scanned. The term "transition" as used herein means a discrete absorption frequency characteristic of a selected molecular gas (or target isotopologue) defined by the difference in energy levels being probed by the excitation laser. The terms "dither" or "dithering" as used herein refer to a sinusoidal variation in current added in the modulation device to a DC current offset and a linear ramp current resulting in a variation in laser frequency that is smaller (10 times to 20 times lower) in amplitude compared to a total range being scanned [e.g., ½ wavenumber ($cm^{-1}$)] and on a time scale that is faster (at least a factor of 5 greater) than the frequency of the repetitive current ramp. For example, if the linear current ramp is repetitively ramped (cycled) at 50 kHz, the dither frequency may be 250 kHz or greater.

Lasers

Continuous wave lasers 4 suitable for use may include, but are not limited to, e.g., Quantum Cascade (QC) lasers, Distributed Feedback (DFB) lasers, Inductively Coupled (IC) lasers, External Cavity (EC) QC lasers, diode lasers, including combinations of these various lasers.

Laser 4 may be contained within a Dewar vessel 8 that maintains a stable temperature for laser 4. In some embodiments, laser 4 may be cooled, e.g., with liquid nitrogen, or with a thermo-electric cooler (not shown). Temperatures may be selected that assist the shift in laser beam frequencies to a desired region of interrogation. In some embodiments, excitation beam 6 delivered by excitation laser 4 may be modulated with a sine wave at a modulation index that is less than or equal to the Doppler width of the molecular absorption line widths. The term "modulation index" as used herein is defined as the frequency range over which a sine wave varies the excitation laser 4.

Spatial Filtering

Figure 2A:
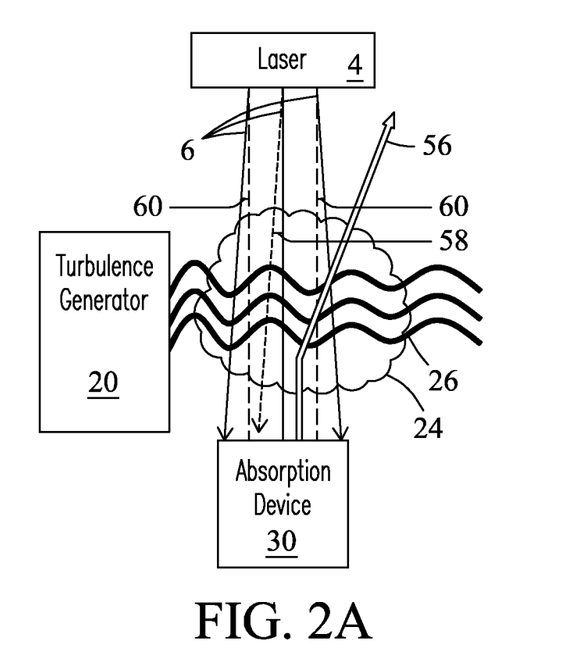
FIGS. 2a-2c show different generators used as components of an optical isolation device, according to different embodiments of the present invention.

Laser beam 6 transmitted from laser 4 may be focused in concert with various spatial filtering devices including, e.g., focusing lenses 10 and 12, slits 14, pin holes 16, distributed feedback (DFB) gratings, including combinations of these various devices. Spatial filtering devices may be further used to suppress reflections of light back to excitation laser 4. Eliminating reflected light may eliminate feedback noise in the absorption signal. For example, spatial filters including, e.g., slits 14 and pin holes 16 may be positioned at a tilt angle that selects a subset of rays from excitation beam 6 at a selected pointing angle (defined by an angle phi) and selected beam spread defined by a divergence angle (theta) into the absorption (transmission) device 30. "Pointing angle (phi)" as used herein is an angle representing the angular variation from the central axis of laser beam 6, described further in reference to FIG. 2. "Divergence angle (theta)" as used herein refers to the angle at which the laser beam diverges or converges from the central axis that defines the spread of the of laser beam 6. "Central axis" as used herein means the optical axis of the laser 4.

In some embodiments, lenses 10 and 14 may be collimating (focusing) lenses that deliver excitation beam 6 from laser 4 such that the excitation beam 6 is delivered off-axis (i.e., at an angle that is offset from the central axis of excitation beam 6) into absorption (transmission) device 30.

In some embodiments, lens 10 may be an external aspheric (e.g., F/1) lens constructed of a transmission material such as zinc selenide (ZnSe) that includes a broadband anti-reflective (AR) coating configured to transmit wavelengths from about 0.6 μm to 16 μm suitable for medium wavelength infra-red (i.e., MWIR) operation.

In some embodiments, excitation beam 6 may be extracted through an off-axis pin hole 16 to absorption device 30 that suppresses feedback noise back to excitation laser 4.

In some embodiments, lens 14 may be a plano-convex, AR-coated silicon (Si) lens (e.g., 50-mm focal length, with >98% bandpass in the MWIR) positioned, e.g., in front of pin hole 16 (e.g., ~1.5-mm diameter), but lens types are not intended to be limited thereto.

Optical Isolation

Figure 2B:
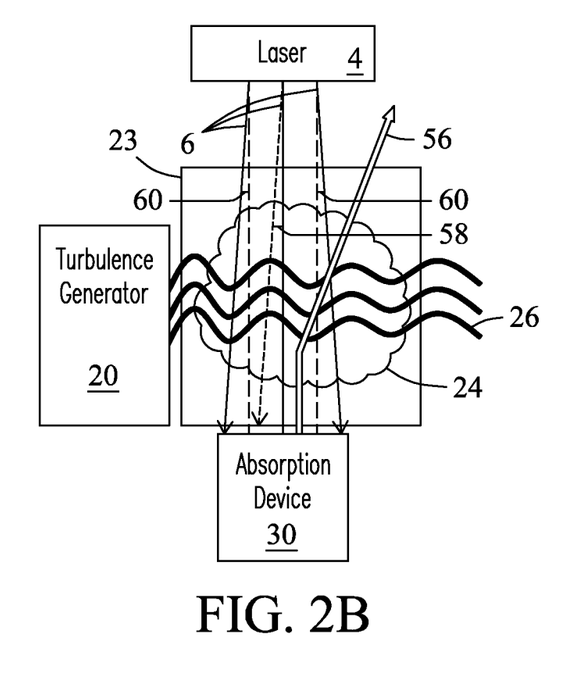
Figure 2C:
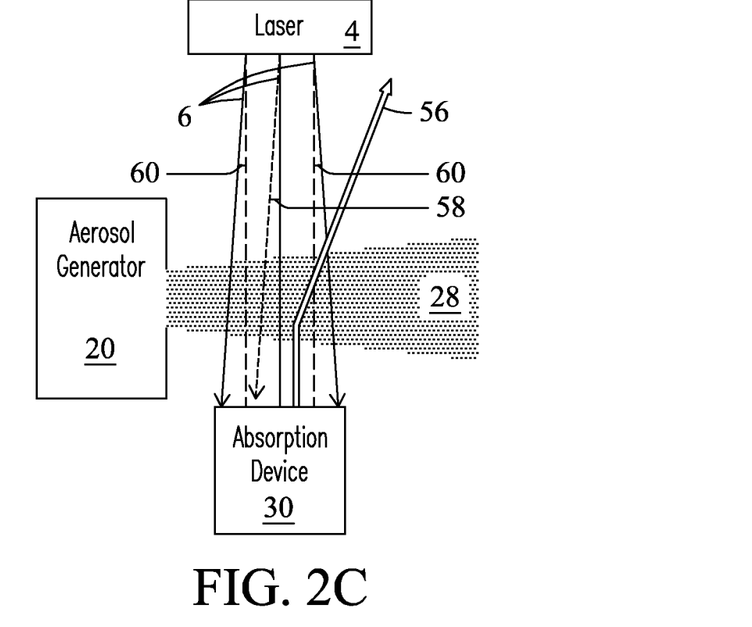

Laser 4 may be coupled to an optical isolation device 18 positioned between excitation laser 4 and absorption device 30 (discussed further in reference to FIGS. 2a-2c herein). "Optical Isolation Device" as used herein means a device that delivers turbulence 26, e.g., through a medium 24 or turbulence to elements present within the medium 24 as a function of time. The term "turbulence" as used herein refers to random spatial and temporal variations introduced in the medium through which the laser beam traverses or that is delivered across the propagation path of the laser beam that alters the index of refraction of the medium. The spatial and temporal variations prevent light from reaching the excitation laser when reflected from the absorption device reaching back to the excitation laser. Turbulence may be induced in concert with various gradients in the medium that introduce variations across the propagation path of the light beam from the laser en route to the absorption (transmission) device. The term "gradient" used herein means a randomly varying distribution of elements (e.g., particulates) present within the medium that introduce variations in the propagation path of the light beam. Gradients include, but are not limited to, e.g., velocity gradients, temperature gradients, heat gradients (i.e., gradients defined by a random distribution of heat waves), density gradients, sonic gradients, aerosol gradients, particulate gradients, and/or other gradients.

Medium 24 may be a fluid medium, a gaseous medium, a liquid medium, an aerosol-containing medium, a particulate-containing medium, or combinations of these various media. Medium 24 may be an open medium an enclosed medium. For example, in some embodiments, medium 24 may be contained within an enclosure 23 or vessel 23. Elements in medium 24 may include, e.g., liquids, gases, particulates, aerosols, heat waves, sonic waves, and like elements that can define a gradient.

"Optical isolation" as used herein refers to the process whereby the excitation laser may be isolated from reflected light that returns back to the excitation laser stemming from an optically coupled absorption (or transmission) device. Reflected light introduces feedback noise into the absorption (transmission) spectrum. Optical isolation in concert with the present invention may be achieved by inducing random spatial (i.e., 3-D positions in space) and temporal (time) variations in the index of refraction of a medium positioned between the excitation laser and the absorption (transmission) device. These random variations may be introduced by a turbulence generator into the medium across the propagation path through which the laser beam traverses en route to the absorption device, or a particulate (e.g., aerosol) generator that disperses particles of varying size and velocity in the medium through which the light beam from the excitation laser is delivered that randomizes the pointing angle and the spread of the light beam as a function of time while the light beam is en route to the absorption (or transmission) device. The turbulence or particulates prevent feedback noise from appearing in the resulting absorption spectrum (see FIG. 7).

Optical Isolation Device 18 may be configured to scatter light delivered from laser 4 through medium 24 en route to capillary waveguide 30 detailed hereafter such that light incident upon, and reflected from, the capillary waveguide 30 experiences scattering conditions and shifts in the pointing angle and beam spread that are different than conditions present for the incident light. The change in pointing and beam spread may serve to isolate laser 4 from reflected light, which serves to suppress optical feedback and resulting feedback noise in the absorption spectrum.

In particular, turbulence may yield a random spatial and temporal variation in the index of refraction of medium 24 or a selected gradient in delivery medium 24 that may suppress feedback noise induced by reflection of the excitation beam 6 incident upon, and from within, the absorption device 30 back to excitation laser 4. Turbulence induced in the medium may provide a signal-to-noise ratio (SNR) enhancement of at least about a factor 2 or better.

Optical isolation device 18 may include a turbulence generator 20 or randomization device that generates turbulence 26 in a medium (open or enclosed) 24 across the propagation path through which the laser beam 6 traverses en route to absorption device 30.

Turbulence Generators

Turbulence generators 20 may include, but are not limited to, e.g., heat sources, gas sources, forced gas sources, flowing gas sources, aerosol devices, nebulizing devices, flame sources, sonic sources, liquid sources, forced liquid sources, flowing liquid sources, including combinations of these various devices.

In some embodiments, the turbulence generator may be a heat gun configured to deliver a random spread or distribution of heat waves of varying temperature across the propagation path of light beam.

In some embodiments, turbulence generator may be coupled to an enclosed liquid through which the light beam is directed that provides the variation in the index of refraction of the light beam when delivered from laser device to absorption (or transmission) device when directed through the liquid.

In some embodiments, the randomization source may be an aerosol generator configured to deliver a random spread of aerosols or particulates dispersed in the medium with a random distribution of sizes and velocities as a function of time across the propagation path of the light beam that is delivered through the volume of aerosols to the absorption (or transmission) device that induces random spatial and temporal variations in the scatter of the beam as it passes through the aerosols or particulates in the medium while en route to the absorption (transmission) device. In some embodiments, the turbulence generator may be a vapor-nebulizing device. In some embodiments, the randomization source may be a sonic device configured to deliver a random spread of sonic waves at a plurality of temperatures above ambient across the propagation path of the light beam from the laser that provides the random spatial and temporal variation in the medium when the light beam is delivered through the spread of sonic waves to the absorption device and/or the transmission device.

Absorption Device

The LA-CAS spectrometer 100 may also include an absorption (or a transmission) device 30 such as a hollow waveguide.

In some embodiments, absorption device 30 may be a capillary waveguide configured to receive a sample gas for analysis containing analytes that absorb (or transmit) in the infra-red wavelength region when an excitation beam from an excitation laser is introduced into the sample gas therein.

In some embodiments, the waveguide may have an internal diameter (I.D.) that is 1-mm and a length that is 0.8 meters. However, dimensions are not intended to be limited. In some embodiments, the waveguide may have an internal diameter that is constant. In some embodiments, the waveguide may be of a tapered design, with an internal diameter that varies as a function of length (i.e., one end has a smaller diameter than the other end) to suppress noise from reflections within the capillary.

In some embodiments, gas volumes in the absorption (transmission) device may below about 0.6 $cm^3$. In other embodiments, gas volumes may be greater than about 0.6 $cm^3$. No limitations are intended.

In some embodiments, waveguide 30 may include coatings optimized for selected laser wavelengths.

In some embodiments, waveguide 30 may include Louisville optics, e.g., as detailed by Harper et al. in Laser-based Spectroscopic Detection Techniques, U.S. Pat. No. 7,102,751, which reference is incorporated herein in its entirety.

Capillary waveguide 30 can allow analyses of samples at total gas pressures below about 25 Torr (0.03 atm), more preferably below about 2 Torr (0.003 atm), and yet more preferably between about 1 Torr (0.001 atm) and 2 Torr (0.003 atm).

Absorption device 30 may also include transmission windows 32 and 38 positioned at respective ends of absorption device 30 that deliver selected IR wavelengths that are absorbed by analytes in absorption device 30 that provide for analysis of these analytes.

In various embodiments, the waveguide may be a capillary waveguide that includes IR transmission windows composed of, e.g., ZnS that transmit wavelengths from about 0.6 μm to 16 μm. In some embodiments, the transmission windows may be composed of sapphire that transmits wavelengths in the range from about 0.15 μm to 5 μm. In other embodiments, transmission windows may be made of other transmission materials known in the art may be that transmit IR wavelengths within selected and suitable ranges for absorption by analytes in the waveguide. All transmission materials as will be selected by those of ordinary skill in the art in view of the disclosure are within the scope of the invention. No limitations are intended.

Absorption device 30 may be coupled to low-dead-volume or vacuum tees 34 and 40 and vacuum valves 36 and 42 that allow sample gases and analytes to be introduced into waveguide 30 and exchanged from waveguide 30 for absorption measurements therein.

In some embodiments, a gas inlet 48 may be employed to provide gas transfer rates into absorption device 30 at low inlet pressures, e.g., between about 0.5 Torr ($7 \times 10^{-4}$ atm) and about 20 Torr (0.03 atm). Inlet 48 may be of a small dead volume design to provide gas-tight operation into waveguide 30. Gas inlet 48 may couple to any of a variety of instrument systems including, but not limited to, e.g., gas chromatographs (GC), laser-ablation and catalytic reactor devices detailed further herein, and other analytical devices. No limitations are intended.

In some embodiments, waveguide 30 may be operated in a static mode. In some embodiments, waveguide 30 may be operated in a continuous (dynamic) mode.

For example, in some embodiments, outlet valve 36 may couple to a vacuum system (not shown) allowing exchange of static samples or a controlled continuous flow of a sample in a dynamic or a continuous sampling mode at selected and selected and/or suitable vacuum pumping speeds and gas transfer rates. Position of valves in the present invention is not intended to be limited to exemplary embodiments described herein.

In some embodiments, waveguide 30 may be coupled to a laser ablation device and a catalytic reactor as detailed hereafter, which permits conversion of solid samples into molecular gases suitable for absorption measurements within waveguide 30.

Laser Ablation and Catalytic Combustion Conversion

Spectrometer (LA-CAS) 100 may include a laser ablation device 44 coupled with a catalytic (or combustion) reactor 46 that provides ablation of solid samples and conversion of the ablated particulates forming molecular gases. The molecular gases may be introduced to absorption device 30 for analysis in spectrometer (LA-CAS) 100.

Detector

The LA-CAS spectrometer (LA-CAS) 100 may also include a detector 52 that is coupled to absorption device 30 and to a detection device 54 configured to detect absorption features for one or more analytes in a sample gas when introduced into absorption device 30. The detector transmits absorption (transmission) signals. Detectors suitable for use may include infra-red sensitive detectors such as indium-antimonide (InSb) detectors configured to produce an output current that is proportional to the intensity of the laser light transmitted from the absorption device that is now incident on the detector resulting from detection of absorption (transmission) signals generated in the waveguide during analysis.

Turbulence Generator Operation

FIG. 2a shows a turbulence generator 20 coupled to a medium 24 containing a gas dispersed in an open volume. In the figure, turbulence generator 20 induces turbulence in the gas 24 by delivering random thermal and velocity gradients across the propagation path of excitation beam 6 delivered through the gas in the open medium 24. In some applications, turbulence may be induced in the gas by delivering heated and turbulent air from the generator. In the figure, excitation beam 6 may be delivered through medium 24 to absorption device 30. When delivered through the turbulent medium, laser beam 6 may be spread from a parallel delivery path by a distance defined by a divergence angle (theta) 60. Any reflected light 56 from absorption device 30 must pass through medium 24 again. The random spatial and temporal variations in the index of refraction of the medium 24 due to the induced turbulence ensures that laser beam divergence angle (theta) 60 and laser beam 6 pointing angle (phi) 58 are different for reflected light 56, which prevents reflected light 56 from being incident on laser 4 and prevents feedback-induced noise in the absorption spectrum.

FIG. 2b shows a turbulence generator 20 (e.g., a sonic generator or a heat generator) coupled to an enclosed volume 24 containing, e.g., an enclosed fluid or an enclosed gas. Again, turbulence generator 20 induces turbulence in the fluid or gas contained within the enclosed volume 24 that delivers, e.g., random sonic and/or thermal agitation in the enclosed medium 24. In the figure, excitation beam 6 may be delivered through medium 24 to absorption device 30. When delivered through the turbulent medium 24, laser beam 6 may be spread from a parallel delivery path by a distance defined by a divergence angle (theta) 60. Any reflected light 56 from absorption device 30 must pass through medium 24 again. Random spatial and temporal variations in the index of refraction of medium 24 containing the gas due to the induced turbulence ensures that laser beam 6 includes a divergence angle (theta) 60 and a pointing angle (phi) 58 that are different for the reflected light 56, which prevents reflected light 56 from being incident on laser 4 and prevents feedback-induced noise in the absorption spectrum.

FIG. 2c shows a generator 22 of an aerosol or particulate delivery design used as a component of an optical isolation device 18. In the figure, generator 22 is configured to deliver a random spread of aerosols or particulates with a random distribution of sizes and velocities across the propagation path of the light beam 6 when the light beam 6 is delivered to the absorption (or transmission) device 30. For example, when the light beam 6 is directed through the spread of aerosols or particulates in the medium 24, the pointing angle beam 6 and the spread of the light beam as a function of time are randomized. In particular, when the laser beam 6 is delivered through the aerosols or particulates in the medium, any reflected light 56 from absorption device 30 must pass through the medium 24 again. The random distribution of aerosols of various sizes and velocities in medium 24 ensures that the divergence angle (theta) 60 and the pointing angle (phi) 58 of laser beam 6 are different for the reflected light 56, which prevents reflected light 56 from returning back to the laser 4, thereby preventing feedback-induced noise in the absorption spectrum.

Conversion of Solid Samples

Figure 3:
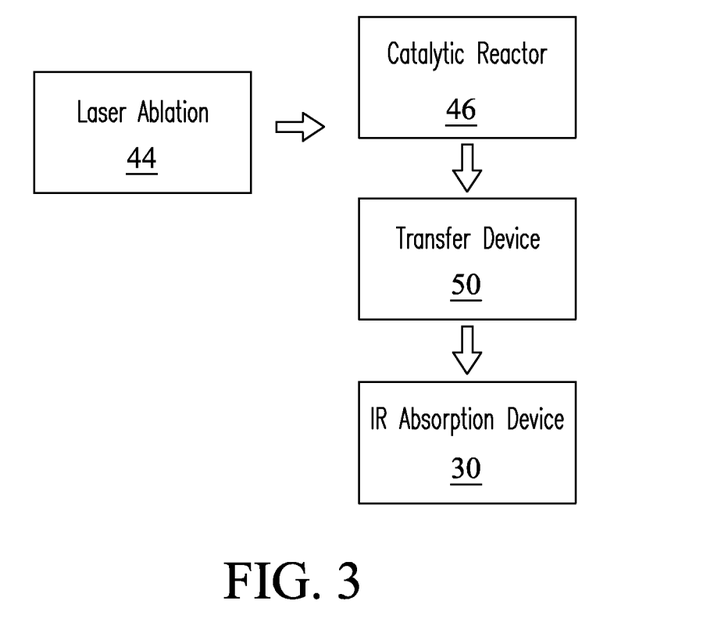
FIG. 3 shows devices that convert solid samples to molecular gases analyzed in the spectrometer of the present invention.

FIG. 3 shows exemplary devices that may be coupled to CAS 100 to convert solid samples into molecular gases suitable for analysis by the present invention. As shown in the figure, CAS 100 may further include a laser ablation device 44 that couples to a catalytic reactor 46. Laser ablation device 44 may ablate the sample (including, e.g., biological materials) and form sample particulates, e.g., as detailed by Moran et al. (*Rapid Commun. Mass Spectrom.* 2011, 25, 1282-1290), which reference is incorporated herein in its entirety. Ablated sample particulates from ablation device 44 may be delivered through a catalyst in catalytic reactor 46, which converts the particulates into a molecular gas containing isotopologues representative of the ablated sample. Molecular gases formed in reactor 46 may be subsequently transferred via a transfer device 50 (described further herein in reference to FIG. 4 and FIG. 5) into the wave guide 30 for determination therein. Sample particulates may be combusted forming gases that may be analyzed at pressures below 25 Torr (0.03 atm). Molecular gases stemming from the converted and combusted sample may be transferred through a transfer device detailed hereafter to the capillary absorption device 30 (described previously in reference to FIG. 1) for analysis.

Cryogenic Transfer Devices

Figure 4A:
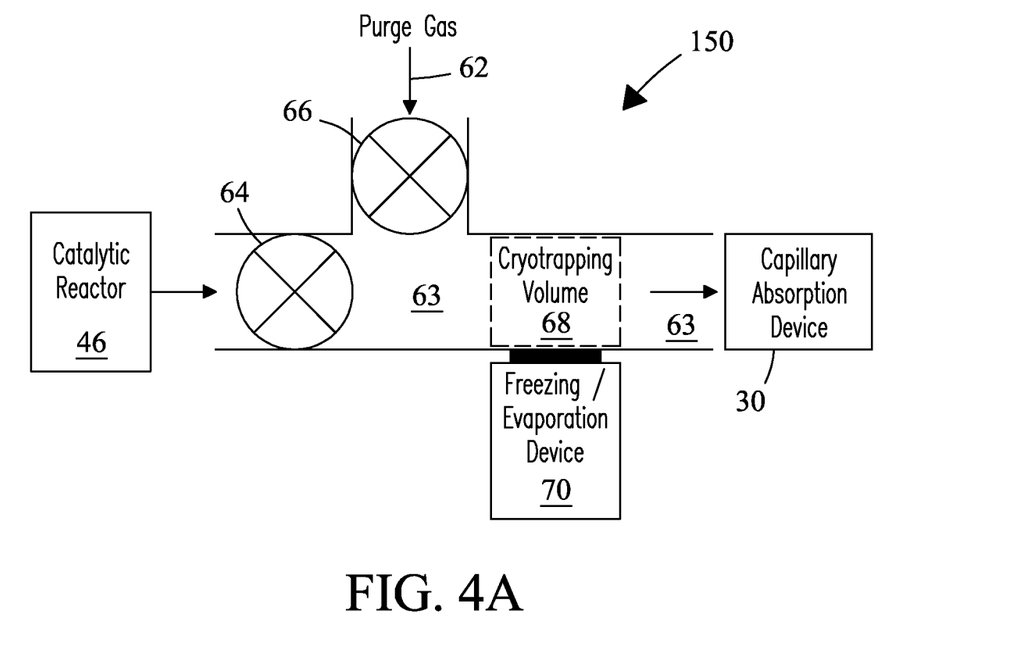
FIGS. 4a-4b show transfer devices of a cryogenic design used in concert with the present invention.

FIG. 4a shows one embodiment of a transfer device 150 of a cryogenic design configured to transfer (deliver) analytes in a molecular gas from a catalytic reactor 46 at a first (e.g., high) pressure and deliver the analytes in the molecular gas into absorption device 30 at a second (lower) pressure without loss of analytes. Transfer device 150 may include a cryogenic trap 63 with a trapping volume 68 that is configured: 1) to receive the molecular gas delivered from the catalytic reactor 46, e.g., through a first valve 64 at a first (high) pressure. Trapping volume 68 of cryogenic trap 63 may be coupled, e.g., to a condensing (freezing)/evaporation device 70 that condenses and traps the analyte-containing molecular gas. For example, in the cryo-trapping phase, valve (V1) 64 may be opened to receive a flow of gas from catalytic reactor 46 into trapping volume 68 of cryogenic trap 63 at a temperature below the freezing point of the molecular gas such the sample gas is condensed, frozen, and trapped as a solid therein while allowing a carrier gas such as helium (He) with a higher freezing temperature to flow through the trap 63. A purge and/or carrier gas 62 such as helium (He) may be introduced into cryogenic trap 63, e.g., through a second valve (V2) 66 to assist with transfer of sample gases from trapping volume 68 to capillary absorption spectrometer 30. Valve (V1) 64 may be closed and trapping volume 68 containing the cryogenically trapped sample may be evacuated (e.g., through a vacuum system valve of the LA-CAS described in reference to FIG. 1) to remove excess carrier gas that yields a lower pressure, e.g., between about 1 Torr (0.001 atm) and about 25 Torr (0.03 atm) suitable for introduction of the molecular gas into capillary absorption device 30 for analysis therein. In this manner, analytes in cryogenic trap 63 may be isolated to give gas pressures in trap 63 that match the second (lower) pressure of absorption device 30. Following evacuation, valve 36 to vacuum system may be closed and freezing/evaporation device 70 may heat the cryotrapped gas in trapping volume 68 above the evaporation temperature of the molecular gas, allowing it to fill absorption spectrometer 30 at the second (lower) pressure. Pressures suitable for use in the transfer device are not intended to be limited. However, pressures may include a first (high) pressure of from about 760 Torr (1 atm) down to 100 Torr (0.13 atm). Second pressure may be a pressure below about 25 Torr (0.03 atm). In the instant configuration, cyrotrapping volume 68 of cryogenic trap 63 is separate and distinct from the capillary absorption spectrometer 30 volume.

Figure 4B:
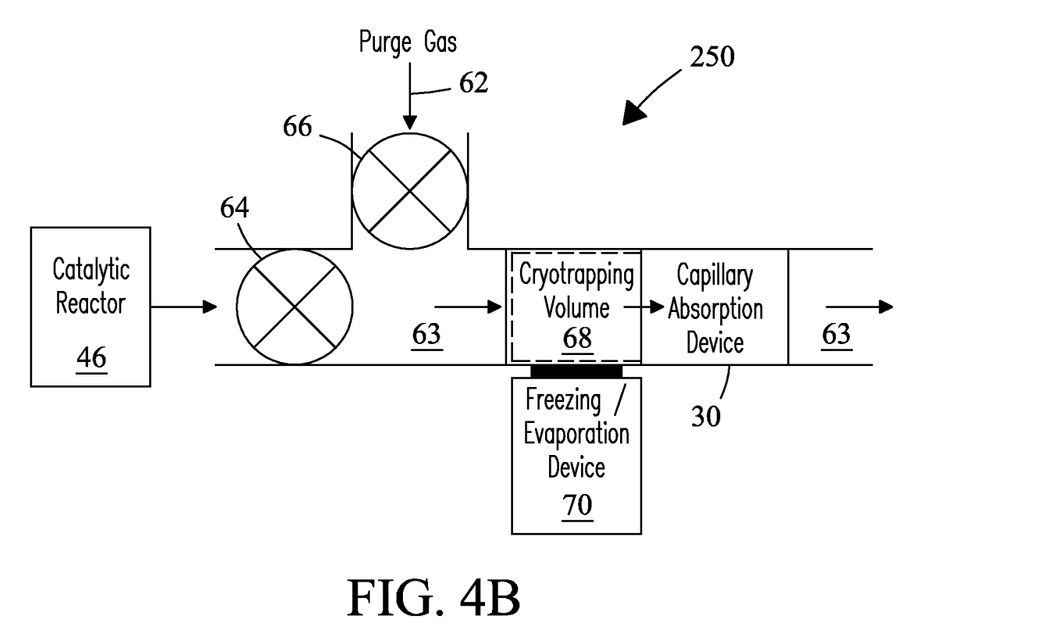

FIG. 4b shows another embodiment of a cryogenic transfer device 250 of the present invention. In this embodiment, freezing/evaporation device 70 is positioned in thermal contact with a selected section or portion of capillary waveguide 30 such that the trapping volume 68 of cryogenic trap 63 is positioned within, and at the leading end of, capillary waveguide 30 to provide cryotrapping of the molecular gas in that section or portion of capillary waveguide 30. In the present embodiment, the capillary waveguide 30 functions both as the transfer device at the first high pressure and the capillary waveguide 30 at the second lower pressure. The present embodiment eliminates potential for introducing dead volumes during the evaporation phase immediately prior to analysis which can reduce molar sensitivity or diluting the cryotrapped sample that can result from addition of an extra volume external to capillary waveguide 30. All other components and operation are as detailed above for FIG. 4a.

Conduction-Limited Transfer Devices

Figure 5A:
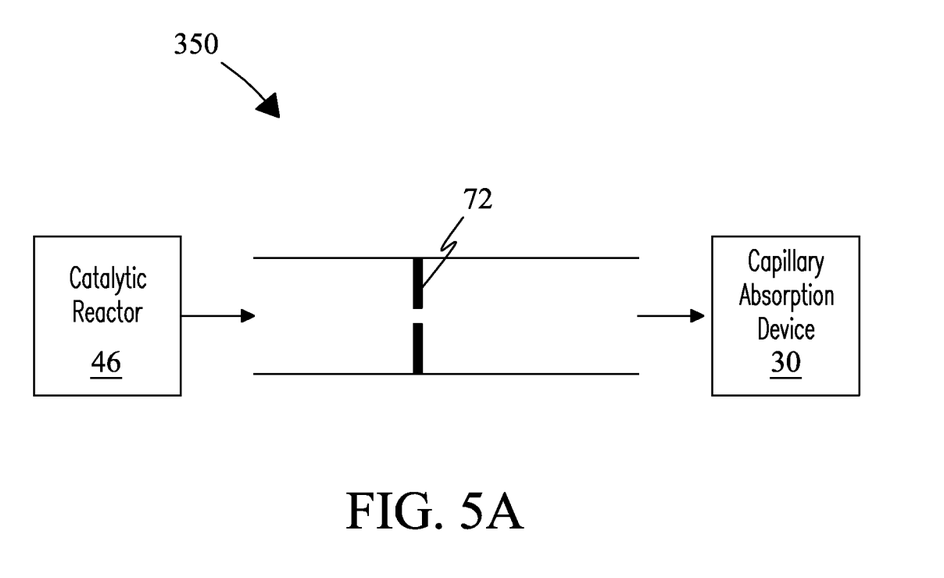
FIGS. 5a-5b show transfer devices of a conduction limited design used in concert with the present invention.

FIG. 5a shows yet another embodiment of a transfer device 350 of a conduction-limited design configured to deliver analytes in a molecular gas from a catalytic reactor 46 at a first (e.g., high) pressure and deliver the molecular gas containing the analytes into absorption device 30 at a second (lower) pressure without a loss of analytes. Pressures suitable for use are not intended to be limited, as detailed hereinabove. Transfer device may include a pin hole (orifice) 72 positioned to impose a conductance barrier for transfer of molecular gases between two different pressures, e.g., a first high pressure and a second lower pressure. Dimensions of pin hole 72 are not limited, and may be selected such that molecular gases are transferred through pin hole 72 at a selected rate and at a selected pressure into absorption device 30. For example, transfer of the gas through the pin hole 72 reduces pressure of the gas from the first high pressure to the $2^{nd}$ lower pressure such that it is compatible with the inlet pressure into absorption device 30 at the lower pressure.

Figure 5B:
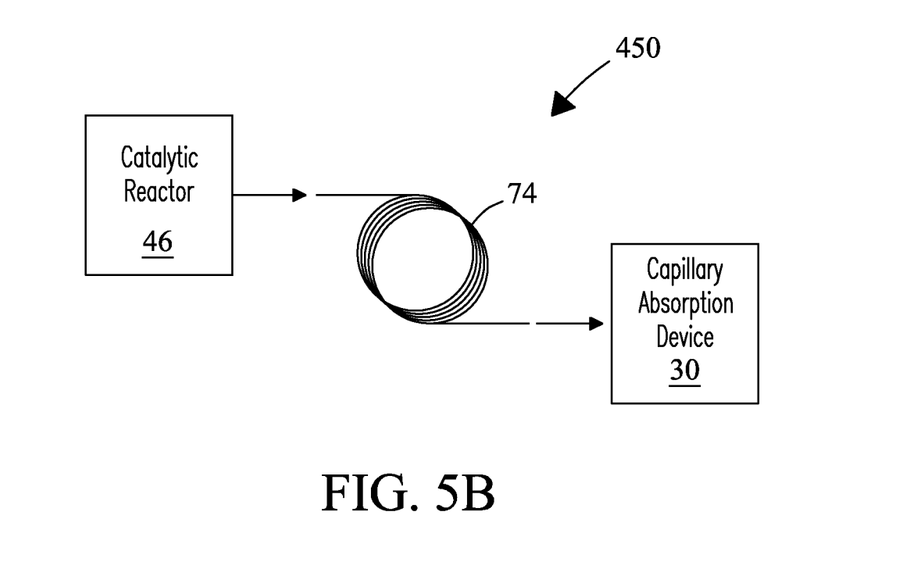

FIG. 5b shows yet another embodiment of a conduction-limited transfer device 450 that operates under a graded pressure reduction regime, providing continuous transfer of analytes from the catalytic reactor 46 to the absorption device 30. In the figure, transfer device 450 has the form of a capillary tube 74 positioned to impose a conductance barrier for transfer of molecular gases between two different pressures, e.g., a first high pressure and a second lower pressure. Length and internal diameter dimensions of capillary tube 74 are not limited, and may be selected such that analytes in the molecular gas received from catalytic reactor 46 may be transferred into capillary tube 74 at a selected rate and at a first high pressure, and then undergo a selected and graded pressure reduction, and then to exit capillary tube 74 at a second (lower) pressure compatible with introduction into IR absorption device 30. Analytes may be continuously transferred at selected rates from catalytic reactor 46 to IR absorption device 30 for analysis.

Modulation Circuit

Figure 6:
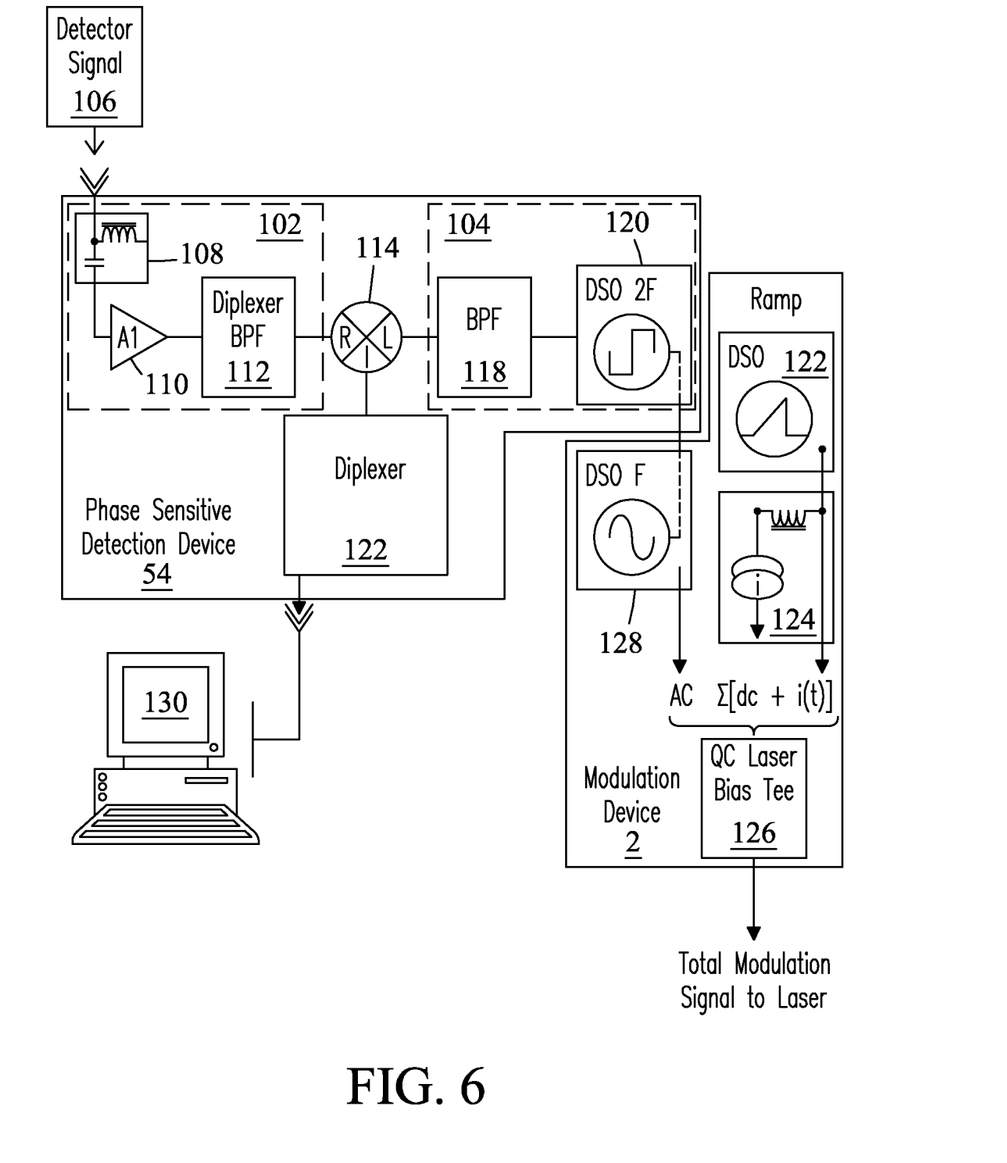
FIG. 6 shows schematics of an exemplary detection device coupled to a modulation device used in concert with the present invention.

FIG. 6 shows a schematic of a (signal) modulation device circuit 2 of LA-CAS 100. Modulation device 2 may be configured to modulate the wavelength of excitation beam 6 delivered by excitation laser 4, which modulations may be delivered as outputs to excitation laser 4. Modulation device 2 may include a linear current ramp source 122 [e.g., a Digital Signal Oscillator (DSO)] that provides a repetitive linear ramp current to a DC power (offset) (summing) device 124. The DC offset device 124 provides a DC offset current. The linear current from the linear current source 122 determines the wavelength range over which the laser frequency is scanned. The value of the DC offset current determines the starting value of the laser frequency in the frequency scan. The maximum value of the current from the linear current ramp source 122 determines the ending value of the laser frequency scan. The slope of the current from the linear ramp device 122 may determine the rate at which the laser frequency is scanned. The DC offset device 124 then sums the linear ramp current obtained from the linear current source 122 together with the DC offset current from the DC offset device 124, e.g., as detailed by Taubman et al. in U.S. Pat. No. 7,957,441, which reference is incorporated in its entirety herein.

Modulation device 2 may further include a dither-modulated current source 128 [e.g., a DSO] that delivers a dither-modulated current (e.g., AC delivered at 1f) as an output in which the frequency of the modulated current is ½ the in-quadrature condition of a residual amplitude modulation distortion frequency (response) of excitation laser 4. The term "in-quadrature" as used herein means the frequency oscillations (modulations) in the excitation beam differ or are separated in phase by 90° ($\pi/2$ radians or $\lambda/4$) from the amplitude oscillations (or modulations). In some embodiments, dither-modulated current source 128 may be operated at frequency (f) that includes a crossover frequency near 95 kHz, e.g., as detailed by Kelly et al. [*Review of Scientific Instruments*, 83, 023101 (2012)]. No limitations are intended.

Driving Circuit

The output (AC) from the dither-modulated current source [DSO F] 128 may be combined with the repetitive linear ramped current delivered from the linear current ramp source [DSO] 122 along with the DC offset current from the DC offset source 124 and provided as an output to a $2^{nd}$ order or higher Bias-Tee (diplexer) 126 positioned in modulation device 2. Bias-Tee (diplexer) 126 may deliver a combined, summed, and thus total modulated current signal to excitation laser 4 as a function of time. Bias-tee 126 may also suppress harmonics from the repetitive linear current ramp source 122 and sub-harmonics from the dither-modulated current source 128 such that the amplitude of the harmonics and sub-harmonics is at least 60 dB lower than the total modulated current waveform selected and provided to excitation laser 4. The term "harmonic" means an integer multiple of a fundamental oscillation frequency delivered by a signal oscillator that may cause undesired noise in a detected signal. The term "sub-harmonic" means a fraction of the fundamental oscillation frequency delivered by a signal oscillator that may cause undesired noise in a detected signal.

Phase-Sensitive Detection Device Circuit

FIG. 6 further shows a phase-sensitive detection device circuit 54 that couples with modulation device circuit 2. Phase-sensitive detection circuit 54 suppresses noise in the absorption signal arising from the RAM distortion frequency received from excitation laser 4 and from harmonic distortion frequencies received from dither-modulated current source 128. Phase-sensitive detection circuit 54 may include a first circuit segment (leg) 102 having a diplexer/band-pass filter 112 of a $2^{nd}$ or greater order that delivers a detection signal 106 from absorption device 30 as an input to a double-balanced mixing device 114. First circuit segment 102 may also include a bias-tee 108 of a $2^{nd}$ or greater order configured to receive the detection (absorption) signal 106 from the detector (FIG. 1). Detection signal 106 may be amplified, e.g., with a pre-amp device 110 prior to being introduced to diplexer/bandpass filter 112 that filters out amplification noise from detection signal 106 before it is introduced to double mixing device 114.

Phase-sensitive detection circuit 54 may also include a second circuit segment (leg) 104 that includes a Band-Pass Filter (BPF) 118 configured to deliver a reference (drive) signal free of harmonic and intermodulation distortion as a separate input to double-balanced mixing device 114.

In some embodiments, the reference drive signal delivered to the bandpass filter 118 may be at a frequency (i.e., 1f) provided by the dither-modulated current source 128 that is ½ the frequency for the in-quadrature condition of the residual amplitude modulation distortion frequency (response) of excitation laser 4. The term "1f" refers to the drive frequency of the dither-modulated current source 128. Signal recovery can be achieved at (1f) when the amplitude of the laser device is constant over the wavelength range being scanned. Thus, no limitations are intended.

In some embodiments, a $2^{nd}$ DSO device 120 may be inserted between device [DSO F] 128 and bandpass filter 118 to deliver a reference or drive (2f) signal [e.g., for (2f) signal recovery] to bandpass filter 128 at a frequency (i.e., 2f) that is 2 times the frequency provided by the dither-modulated current source [DSO F] 128. The 2f drive frequency provided by DSO 120 device may be synchronized such that it is in-phase with the output (1f) frequency delivered from dither-modulated current source 128. The term "2f" (or second harmonic detection or Waveform Modulated detection) refers to a drive frequency or a detection frequency that is twice the magnitude of the reference frequency delivered from the dither-modulated current source 128. A (2f) frequency may be used when the amplitude of the intensity of the laser beam is not constant over the wavelength range being scanned in order to eliminate slope in the baseline, delivering a flat baseline in the detection signal.

Double-balanced mixing device 114 may then deliver an output signal made up of various combinations of signals (i.e., mixed signals) received from the respective inputs. For example, double-balanced mixing device (DBM) 114 may couple to a $2^{nd}$ or greater order diplexer (bias-T) 122 configured to: 1) receive the mixed output signal from the DBM 114 as an input and 2) to isolate a selected absorption response signal (see discussion FIG. 7) for one or more selected analytes present in the mixed signal. The $2^{nd}$-order or greater Diplexer 122 may be configured to receive an output signal from the double balanced mixing device 114 as an input and to deliver a distortion free response signal as an output at a selected frequency therefrom. In various embodiments, the $2^{nd}$-order or greater diplexer 122 may deliver the absorption response signal isolated from 1-times (1f) or 2-times (2f) the dither-modulated frequency delivered from the dither-modulation device 128 that is also 90 degrees out-of-phase with the RAM distortion frequency provided to excitation laser 4. In some embodiments, the $2^{nd}$-order or greater Diplexer may deliver a response signal with a frequency selected in the range from about 100 Hz to about 30 KHz with an isolation of about 30 dB per decade at the upper cutoff frequency. The isolated response signal may be observed in concert with a CPU 130 or other transient signal recording device.

Results

Figure 7:
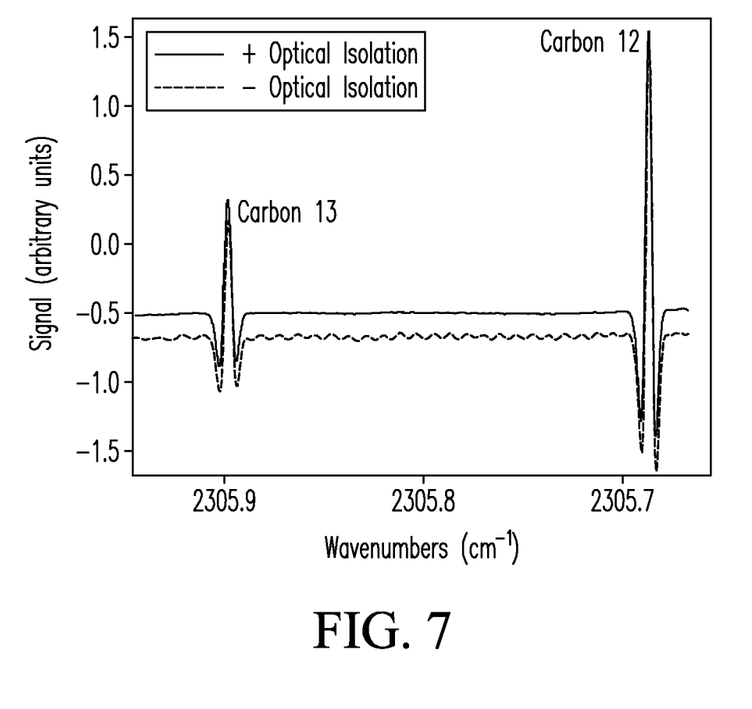
FIG. 7 compares (2f) detection signals for representative isotopes obtained with and without optical isolation of the present invention.

FIG. 7 compares (2f) absorption signals for representative isotopologues of carbon dioxide containing $^{13}C$ and $^{12}C$, respectively, recovered with and without use of the optical isolation device of the present invention. In the figure, signals were obtained at twice the frequency of the dither-modulated current source. Results show the reduction in feedback noise produced by the incident laser beam on the capillary wave guide stemming from reflection from the absorption device back to the excitation laser. Results collected with the optical isolation device (FIG. 1) of the present invention shows that feedback noise is reduced by a factor of at least about 50 compared with results collected absent the optical isolation device. However, reduction factors are not intended to be limited. The reduction factor may be calculated as the ratio of the total integrated intensity of the absorption features to the standard deviation (SD) of variations (noise) observed in the baseline.

Detection Limits

TABLE 1 compares instrumental gas-phase detection limits (DL) of LA-CAS 100 to commercial infrared absorption-based isotopic analyzers using internationally certified isotopic $CO_2$ gas standards.

TABLE 1

Compares molar detection limits and isotopic precisions (‰) at given analysis (dwell) times for isotopic measurements of $CO_2$ of commercial isotopic analyzers compared with the LA-CAS.

| System | Total Volume (mL) | Pressure (Torr) | $CO_2$ Concentration (ppm) | Effective Detection Limit Molar Sensitivity (Moles) | Measured Precision, ‰ and (Dwell Time) |
|---|---|---|---|---|---|
| 1[a] | 30 | 300 | 300 | $1.6 \times 10^{-7}$ | 0.5 (100 sec) |
| 2[b] | 120 | 300 | 300 | $6.4 \times 10^{-7}$ | 0.25 (60 sec) |
| 3[c] | 300 | 25 | 300 | $1.3 \times 10^{-7}$ | 0.2 (1 sec) |
| LA-CAS | 0.63 | 4.0 | 749 | $1.1 \times 10^{-10}$ | 0.6 (10 sec) |
| LA-CAS | 0.63 | 2.5 | 4500 | $4.2 \times 10^{-10}$ | 0.1 (10 sec) |
| LA-CAS | 0.63 | 2.0 | 390 | $2.0 \times 10^{-10}$ | 2 (10 sec) |

[a]Picarro CRDS instrument, E. H. Wahl et al. in "*Isotopes Environ. Health Stud.*" 42, 21 (2006).
[b]Los-Gatos ICOS instrument [http://www.lgrinc.com].
[c]Aerodyne 7.3-meter Herriott cell [see J. B. McManus et al. in "*Isotopes Environ. Health Stud.*", 46, 49 (2010); and D. D. Nelson et al. in "Appl. Phys. B", 90, 301 (2008).

In TABLE 1, isotopic precision (‰) is stated in standard delta ($\delta$) notation used in isotopic measurements, in which stable isotopic compositions of low-mass (light) elements such as oxygen, hydrogen, carbon, nitrogen, and sulfur are normally reported as "delta" ($\delta$) values in parts per thousand (denoted as ‰) enrichments or depletions relative to a standard of known composition. The symbol (‰) is spelled out in several different ways: per mil, per mil, per mill, or per mille. The term "per mill" is the ISO term, but is not yet widely used. Delta ($\delta$) values may be calculated, as given by Equation [1] below:

$$(‰) = (R_{sample}/R_{standard} - 1)1000 \quad [1]$$

Here, "R" is the ratio of the heavy to light isotope in the sample or standard. For the elements sulfur, carbon, nitrogen, and oxygen, the average terrestrial abundance ratio of the heavy to the light isotope ranges from 1:22 (sulfur) to 1:500 (oxygen); the ratio $^2H:^1H$ is 1:6410. A positive ($\delta$) value means that the sample contains more of the heavy isotope than the standard. A negative ($\delta$) value means that the sample contains less of the heavy isotope than the standard. As an example, a $\delta^{15}N$ value of +30‰ means that there are 30 parts-per-thousand (or 3%) more $^{15}N$ isotopes in the sample compared with the standard.

As shown in TABLE 1, LA-CAS 100 of the present invention provides a sensitivity exceeding other infrared absorption detection methods. LA-CAS 100 with 1-mm ID hollow waveguides (HWGs) of nominal 1-m path length can resolve $\delta^{13}C$ variances to less than 1‰ with total sample quantities down to 100 picomoles (pmols) using commercial standards. The LA-CAS has also demonstrated molar sensitivities down to 2 picomoles at 1‰, with projected improvements down to 100 femtomoles.

Applications

The LA-CAS of the present invention enables spatially resolved isotopic imaging in a variety of sample types for fundamental biological and chemical research and forensic applications, including, e.g., thin films, polymers, forensic samples including, e.g., hair (both human and animal), tree growth rings, and microbial systems. And, LA-CAS can be performed on samples under ambient atmospheric conditions that require no preparation beyond mounting the sample. Stable isotope analyses permit tracking of physical, chemical, and biological reactions in various sample materials in physical, biological, and chemical processes, interactions, and mechanisms at various spatial scales ranging from the atmosphere to individual microorganism cells. The LA-CAS may also be configured to study isotopic ratios of $CO_2$ and other gases produced by catalytic combustion of evolved particulates created by UV laser ablation of nonvolatile organics, and can be used to study $CO_2$ and other molecular gases directly from various niche bio-compartments including waste gases generated from soil bacteria and other environments.

The LA-CS also provides highly sensitivity isotope ratio measurements on extremely small samples with volumes less than or equal to about ~0.5 mL.

The present invention also eliminates optical feedback in continuous (CW) Quantum Cascade (QC) lasers.

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

What is claimed is:

1. A method for analyzing low-volume target analytes, comprising the steps of:
   introducing a turbulent gas, liquid, or aerosols through a medium across the propagation path of a laser excitation beam introduced into a capillary infrared absorption device in a capillary absorption spectrometer to provide a picomolar detection sensitivity therein;
   ablating a solid sample containing at least a picomolar quantity of the target analytes therein with a pulsed UV excitation beam to convert the sample into sample particulates;
   transferring the ablated sample particulates to a catalytic reactor;
   converting the ablated sample particulates in the catalytic reactor into a molecular gas;
   transferring the molecular gas from the catalytic reactor through a transfer device at a first higher pressure into the capillary infrared absorption device at a second lower pressure; and
   analyzing the molecular gas in the capillary absorption device with an infrared absorption detector to determine isotopic ratios of the target analytes in the sample at the picomolar detection sensitivity.

2. The method of claim 1, wherein the capillary absorption device has a sample volume below about 10 $cm^3$.

3. The method of claim 1, wherein the analysis is an in vivo analysis performed at ambient pressure and temperature conditions comprising ablation of selected locations of a biological sample that yields an isotopic ratio of the target analytes therein.

4. The method of claim 3, wherein the in vivo analysis yields isotopic images of target analytes in the selected locations of the ablated biological sample that allows tracking (mapping) of the target analytes therein as a function of time.

5. The method of claim 1, further including calibrating the capillary infrared absorption device with a solid sample referenced to a known standard.

6. The method of claim 5, wherein the calibration standard includes a polymer.

7. The method of claim 5, wherein the calibration is performed with a normalization method.

8. The method of claim 3, wherein the biological sample contains a biological material selected from the group consisting of: isolates, cells, microorganisms, microbes, and combinations thereof.

* * * * *